United States Patent
Torii et al.

(10) Patent No.: US 12,136,191 B2
(45) Date of Patent: Nov. 5, 2024

(54) IMAGE PROCESSING APPARATUS, IMAGE PROCESSING METHOD, AND NON-TRANSITORY COMPUTER-READABLE STORAGE MEDIUM

(71) Applicant: CANON KABUSHIKI KAISHA, Tokyo (JP)

(72) Inventors: Sota Torii, Kanagawa (JP); Atsushi Iwashita, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 442 days.

(21) Appl. No.: 17/529,327

(22) Filed: Nov. 18, 2021

(65) Prior Publication Data

US 2022/0076397 A1    Mar. 10, 2022

Related U.S. Application Data

(63) Continuation of application No. PCT/JP2020/016777, filed on Apr. 16, 2020.

(30) Foreign Application Priority Data

May 30, 2019 (JP) .................................. 2019-101483

(51) Int. Cl.
*G06T 7/00* (2017.01)
*A61B 6/00* (2006.01)
(Continued)

(52) U.S. Cl.
CPC .............. *G06T 5/50* (2013.01); *A61B 6/00* (2013.01); *G06T 5/70* (2024.01); *G06T 7/0012* (2013.01)

(58) Field of Classification Search
CPC ........... G06T 7/0012; G06T 7/70; G06T 5/50; G06T 2207/10116; G06T 2207/20224;
(Continued)

(56) References Cited

U.S. PATENT DOCUMENTS 5,485,371 A * 1/1996 Ito ..................... H04N 5/3205
                                                        348/E5.089
7,697,739 B2 * 4/2010 Sakaida ............ G06T 7/0012
                                                         382/128
(Continued)

FOREIGN PATENT DOCUMENTS

JP    H03-285475 A      12/1991
JP    2003180669 A  *   7/2003
(Continued)

OTHER PUBLICATIONS

Jun. 23, 2020 International Search Report in International Patent Appln. No. PCT/JP2020/016777.
(Continued)

*Primary Examiner* — Quan M Hua
(74) *Attorney, Agent, or Firm* — Venable LLP

(57) ABSTRACT

An image processing apparatus comprises: an image generating unit configured to generate, by using a radiation energy spectrum, a material characteristic image of a material contained in a plurality of radiation images captured by different radiation energies; and a noise reduction processing unit configured to reduce a noise component of the material characteristic image. The image generating unit uses a composite image obtained from the plurality of radiation images, a first material characteristic image in which the noise component has been reduced, and a composite spectrum obtained from spectra of the different radiation energies to generate a second material characteristic image with reduced noise.

20 Claims, 7 Drawing Sheets

(51) Int. Cl.
*G06T 5/50* (2006.01)
*G06T 5/70* (2024.01)

(58) Field of Classification Search
CPC . G06T 2207/10048; G06T 2207/30008; G06T 5/70; G06T 2207/10152; G06T 2207/10056; G06T 3/4084; G06T 5/00; G06T 5/10; G01N 23/087; H04M 2250/12; G09G 2354/00; G09G 2356/00; G06V 10/225; G06V 10/255; G06V 10/30; G06V 10/88; G06V 10/56; G06V 40/10; G01T 1/171; G01T 1/17; G06N 10/00; G06N 3/044; G06N 3/048; G06N 3/08; G06N 3/084
See application file for complete search history.

(56) References Cited

U.S. PATENT DOCUMENTS

| | | | |
|---|---|---|---|
| 7,760,848 B2 | 7/2010 | DeMan et al. | |
| 7,778,380 B2 | 8/2010 | Altman et al. | |
| 7,873,141 B2 | 1/2011 | Imai et al. | |
| 9,056,644 B2 | 6/2015 | Hudák | |
| 10,182,775 B2 | 1/2019 | Nakai et al. | |
| 10,573,030 B2 | 2/2020 | Keeler | |
| 2006/0235327 A1* | 10/2006 | Masuo | A61B 5/0537 600/547 |
| 2008/0063135 A1 | 3/2008 | DeMan et al. | |
| 2008/0226017 A1 | 9/2008 | Altman et al. | |
| 2008/0260092 A1 | 10/2008 | Imai et al. | |
| 2009/0086907 A1* | 4/2009 | Smith | G01V 5/232 378/57 |
| 2014/0210180 A1 | 7/2014 | Hudák | |
| 2014/0255694 A1* | 9/2014 | Bakke | C22B 26/10 209/552 |
| 2014/0376686 A1* | 12/2014 | Dreiseitel | G01V 5/226 382/304 |
| 2016/0022243 A1 | 1/2016 | Nakai et al. | |
| 2016/0054453 A1* | 2/2016 | Moriyasu | A61B 6/4035 378/19 |
| 2018/0293763 A1 | 10/2018 | Keeler | |
| 2020/0205755 A1 | 7/2020 | Iwashita et al. | |
| 2020/0402275 A1 | 12/2020 | Keeler | |

FOREIGN PATENT DOCUMENTS

| | | |
|---|---|---|
| JP | 2008-062035 A | 3/2008 |
| JP | 2008-125900 A | 6/2008 |
| JP | 2009-506854 A | 2/2009 |
| JP | 2014-210180 A | 11/2014 |
| WO | 2018/187735 A1 | 10/2018 |

OTHER PUBLICATIONS

Shin-ichiro Iwamoto, "X-ray attenuation coefficient in diagnostic imaging," Medical Imaging and Information Sciences, vol. 32, No. 3 (2015), pp. 54-62.

* cited by examiner

IMAGE PROCESSING APPARATUS, IMAGE PROCESSING METHOD, AND NON-TRANSITORY COMPUTER-READABLE STORAGE MEDIUM

CROSS-REFERENCE TO RELATED APPLICATION(S)

This application is a Continuation of International Patent Application No. PCT/JP2020/016777 filed on Apr. 16, 2020, which claims the benefit of Japanese Patent Application No. 2019-101483, filed May 30, 2019, both of which are hereby incorporated by reference herein in their entirety.

BACKGROUND OF THE INVENTION

Field of the Invention

The present invention relates to an image processing apparatus, an image processing method, and a non-transitory computer-readable storage medium, and more particularly to an image processing technique that is used for still image capturing such as general image capturing and moving image capturing such as fluoroscopy in medical diagnosis.

Background Art

In recent years, thickness images of a plurality of materials or an image of a surface density and an effective atomic number image (an example of "a planar distribution related to a material") can be obtained from a plurality of different radiation energy images by using a spectral imaging technique which is an imaging technique that uses the energy information of radiation. Such a thickness image, a surface density image, or an effective atomic number image can be obtained by assuming that the thickness or the like of radiation which has been transmitted through a material will exponentially decay, and inversely calculating from the pixel values of the transmitted radiation.

PTL 1 discloses a technique that improves the image quality of a bone image by smoothing an image of a soft tissue and subtracting this image from an accumulated image.

However, in an estimation operation of a planar distribution related to a material, quantum noise originating from system noise or radiation will propagate during the calculation process, and the output image can contain noise. In the technique disclosed by PTL 1, the estimation operation of a planar distribution is performed by using four simple arithmetic operations, and the effect of beam hardening is not considered. Hence, it can be difficult to quantitatively obtain physical property values.

CITATION LIST

Patent Literature

PTL 1: Japanese Patent Laid-Open No. 3-285475

SUMMARY OF THE INVENTION

The present invention provides an image processing technique that will allow a material characteristic image with reduced noise and good quantitative properties to be obtained.

According to an aspect of the present invention, there is provided an image processing apparatus comprising: an image generating unit configured to generate, by using a radiation energy spectrum, a material characteristic image of a material contained in a plurality of radiation images captured by different radiation energies; and a noise reduction processing unit configured to reduce a noise component of the material characteristic image, wherein the image generating unit uses a composite image obtained from the plurality of radiation images, a first material characteristic image in which the noise component has been reduced, and a composite spectrum obtained from spectra of the different radiation energies to generate a second material characteristic image with reduced noise.

Other features of the present invention will become apparent from the following description of exemplary embodiments with reference to the attached drawings. Note that the same reference numerals denote the same or like components throughout the accompanying drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Figure 1:
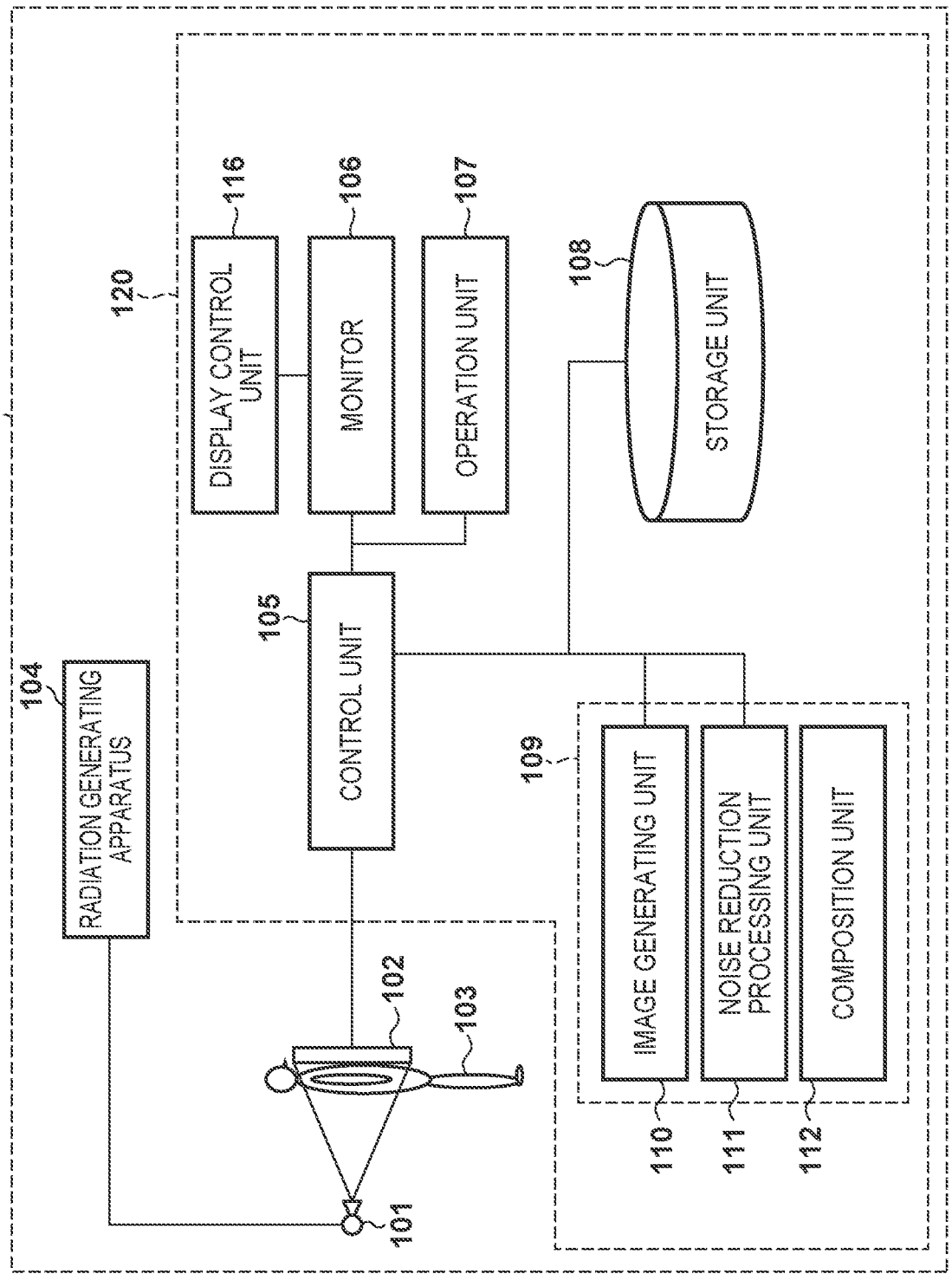
FIG. 1 is a block diagram showing the arrangement of a radiation imaging system according to the first embodiment.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted. In the following embodiments and the appended claims, radiation includes, in addition to X-rays, α-rays, β-rays, γ-rays, and various kinds of particle beams.

First Embodiment

FIG. 1 is a block diagram showing an example of the arrangement of a radiation imaging system 100 according to the first embodiment of the present invention. The radiation imaging system 100 includes a radiation generating apparatus 104, a radiation tube 101, an FPD (Flat Panel Detector) 102, and an image processing apparatus 120. Note that the arrangement of the radiation imaging system 100 may also be simply called a radiation imaging apparatus. The image processing apparatus 120 processes image information based on a radiation image that has captured an object. The image processing apparatus 120 includes a control unit 105, a storage unit 108, an image processing unit 109, a display control unit 116, and the like.

The radiation generating apparatus 104 generates radiation by applying a high-voltage pulse to the radiation tube 101 when an irradiation switch is pressed, and the radiation tube 101 irradiates an object 103 with radiation. Although the type of radiation is not particularly limited, an X-ray can be generally used as used here.

When the object 103 is irradiated with radiation from the radiation tube 101, the FPD 102 obtains a radiation image by accumulating charges based on an image signal. The FPD 102 transfers the radiation image to the image processing apparatus 120.

The FPD 102 includes a radiation detection unit (not shown) in which a pixel array for generating signals corresponding to the radiation is arranged. The radiation detection unit detects radiation that has been transmitted through the object 103 as image signals. Pixels that output signals corresponding to incident light are arranged in an array (two-dimensional region) in the radiation detection unit. A photoelectric conversion element of each pixel converts radiation that has been converted into visible light by a fluorescent material into an electrical signal, and outputs the converted electrical signal as an image signal. In this manner, the radiation detection unit is configured to detect the radiation that has been transmitted through the object 103 to obtain image signals (radiation image). A driving unit of the FPD 102 outputs, to the control unit 105, the image signals (radiation image) read out in accordance with an instruction from the control unit 105.

The control unit 105 includes the image processing unit 109 that processes a radiation image obtained from the FPD 102 and the storage unit 108 that stores the results of image processing operations and various kinds of programs. The storage unit 108 is formed by, for example, a ROM (Read Only Memory), a RAM (Random Access Memory), or the like. The storage unit 108 can store the images output from the control unit 105, the images processed by the image processing unit 109, and the calculation results obtained by the image processing unit 109.

The image processing unit 109 includes, as functional components, an image generating unit 110, a noise reduction processing unit 111, and a composition unit 112. In these functional components, the function of each unit is implemented by one or a plurality of CPUs (Central Processing Units) using a program loaded from the storage unit 108. The arrangement of each unit of the image processing unit 109 may be formed by an integrated circuit or the like as long as a similar function can be achieved. In addition, it may be formed so that a graphic control unit such as a GPU (Graphics Processing Unit) or the like, a communication unit such as a network card or the like, an input/output control unit such as a keyboard, a display, or a touch panel, and the like will be included as the internal components of the image processing apparatus 120.

A monitor 106 (display unit) displays a radiation image (digital image) received by the control unit 105 from the FPD 102 and an image that has been processed by the image processing unit 109. A display control unit 116 can control the display operation of the monitor 106 (display unit). An operation unit 107 can input instructions to the image processing unit 109 and the FPD 102 and accepts the input of instructions to the FPD 102 via a user interface.

The control unit 105 uses an energy subtraction method in which new images (for example, a bone image and a fat image) are obtained by processing a plurality of radiation images which are obtained by irradiating an object with radiation at different energy levels. In a case in which an imaging operation is to be performed by using the energy subtraction method, a plurality of radiation images (for example, at least two radiation images) that have been captured at different radiation energy levels will be needed to generate one subtraction image. The FPD 102 performs a plurality of sampling operations with respect to one radiation irradiation operation. As a result, the FPD 102 can obtain an image (low-energy radiation image) by low-energy radiation and an image (high-energy radiation image) by high-energy radiation in one radiation irradiation operation. The imaging operation by the FPD 102 may be a still-image capturing operation or a moving-image capturing operation.

The radiation distribution information temporarily stored in the FPD 102 can be read out after the execution of a sample-and-hold operation, and the control unit 105 reads out radiation distribution information ($X_L$) and radiation distribution information ($X_L+X_H$) from the FPD 102. The control unit 105 can obtain radiation distribution information ($X_H$) by subtracting the radiation distribution information ($X_L$) from the radiation distribution information ($X_L+X_H$). In this case, the low-energy radiation distribution information ($X_L$) will be a low-energy radiation image (low energy image), and the high-energy radiation distribution information ($X_H$) will be a high-energy radiation image (high energy image).

The image processing unit 109 includes, as functional components, an image generating unit 110, a noise reduction processing unit 111, and a composition unit 112. The image generating unit 110 can generate a plurality of material characteristic images by using a plurality of radiation images captured at different radiation energy levels, and the image generating unit 110 can generate, from the radiation images captured by the FPD 102, material characteristic images such as material separation images and material identification images.

The image generating unit 110 uses a radiation energy spectrum to generate a material characteristic image of each material contained in a plurality of radiation images captured at different radiation energy levels. The image generating unit 110 generates a material characteristic image by using a plurality of radiation images obtained by one radiation irradiation operation.

The noise reduction processing unit 111 executes noise reduction processing to reduce the noise component of each material characteristic image. In addition, the composition unit 112 generates a composite image from a plurality of radiation images (a low energy image and a high energy image). The image generating unit 110 will subsequently use the composite image obtained from the plurality of radiation images (the low energy image and the high energy image), a first material characteristic image which has undergone noise reduction processing, and a composite spectrum obtained from a different radiation energy spectrum to generate a second material characteristic image which has undergone noise reduction.

Material characteristic images are images obtained by separating a plurality of materials contained in the plurality of radiation images (the low energy image and the high energy image), and refer to images separated into two or more images formed based on the thicknesses or densities of the respective materials in a case in which an object is expressed by two or more specific materials. For example, the plurality of materials can include fat as a soft material and bone as a hard material that form the object.

In addition, material identification images are images that show the distributions of the effective atomic numbers and the surface densities of respective materials contained in the plurality of radiation images (the low energy image and the high energy image). In a case in which an object is represented by one specific material, the material identification images will refer to images obtained by decomposing the distribution of the effective atomic number and the distribution of the surface density of this material.

An effective atomic number is a quantitative index that indicates an atomic number of a material corresponding to a case in which an element, a compound, or an element of a mixture is viewed on average, and indicates the atomic number of a virtual element which can attenuate photons at the same ratio as this material. An effective atomic number image refers to an image formed on a pixel basis by an atomic number corresponding to a case in which an object has been represented by one specific material.

Processing performed in the image processing unit 109 according to the first embodiment will be described in detail next with reference to the flowchart shown in FIG. 2. A case in which a plurality of radiation images that were obtained by irradiating an object with different radiation energy levels are processed to be separated into a fat image and a bone image as a plurality of images to be newly obtained will be described here. However, the processing can also be applied to a case in which separation is performed by using another material or a case in which a material identification image is used.

The FPD 102 will execute a plurality of sampling operations with respect to one radiation irradiation operation. As a result, the FPD 102 can obtain a low-energy radiation image (a low energy image 201) and a high-energy radiation image (a high energy image 202) by one radiation irradiation operation. The control unit 105 will store, in the storage unit 108, the radiation images captured by the FPD 102, and transfer the radiation images to the image processing unit 109.

(S210: Generation of Material Characteristic Images)

In step S210, the image generating unit 110 will generate material separation images as the material characteristic images. More specifically, the low energy image 201 ($X_L$) and the high energy image 202 ($X_H$) captured by the FPD 102 will be used by the image generating unit 110 to generate the material separation images based on the following equations (1) and (2).

$$X_L = \frac{\int_0^\infty N_L(E)\exp\{-\mu_B(E)d_B - \mu_A(E)d_A\}EdE}{\int_0^\infty N_L(E)EdE} \quad (1)$$

$$X_H = \frac{\int_0^\infty N_H(E)\exp\{-\mu_B(E)d_B - \mu_A(E)d_A\}EdE}{\int_0^\infty N_H(E)EdE} \quad (2)$$

Where, $\mu$ represents a ray attenuation coefficient, d represents the thickness of a material, E represents radiation energy, N(E) represents a radiation spectrum, suffixes H and L represent high energy and low energy, respectively, and suffixes A and B represent fat and bone, respectively. In equations (1) and (2), the unknown variables are thicknesses $d_A$ and $d_B$. The values of the thicknesses $d_A$ and $d_B$ can be obtained by capturing images (the low energy image 201 ($X_L$) and the high energy image 202 ($X_H$)) based on two different radiation energy levels, substituting the captured images to equations (1) and (2), and solving two independent sets of simultaneous equations.

Note that although fat and bone are used here as examples of materials to be separated, the materials to be separated are not limited to fat and bone, and it is possible to separate arbitrary materials. By solving the simultaneous equations shown in equations (1) and (2) by using an optimization method such as the Newton-Raphson method, the bisection method, or the like to obtain the thicknesses of the respective materials (the thickness $d_A$ of the fat and the thickness $d_B$ of the bone), it will be possible to generate material separation images 203 in which images are separated into a fat image and a bone image as shown in FIG. 2. In the example shown in FIG. 2, the material separation image 203 exemplarily shows a fat image.

(S211: Composition of Radiation Images and Radiation Spectra)

In step S211, the composition unit 112 will generate a radiation image (to be referred as a composite radiation image hereinafter) that has been composited based on the low-energy radiation image (the low energy image 201 ($X_L$)) and the high-energy radiation image (the high energy image 202 ($X_H$)). That is, the composition unit 112 will generate, from the low energy image 201 ($X_L$) and the high energy image 202 ($X_H$), the composite radiation image 204 (Xproc) based on equation (3) as follows. The composition unit 112 executes weighted addition processing on a plurality of radiation images to generate a composite image (the composite radiation image 204 (Xproc)).

$$X\text{proc} = aX_L + bX_H \quad (3)$$

Where, weighting factors a and b are arbitrary positive numbers, and the sum of a and b are set to be 1. For example, the composition unit 112 can calculate the radiation dose or the number of photons during the capturing of the low energy image 201 ($X_L$) and the high energy image 202 ($X_H$), and set, based on the ratio or the radiation dose or the ratio of the number of photons in the plurality of radiation images, the values of the weighting factors a and b in the addition processing of equation (3).

Figure 3:
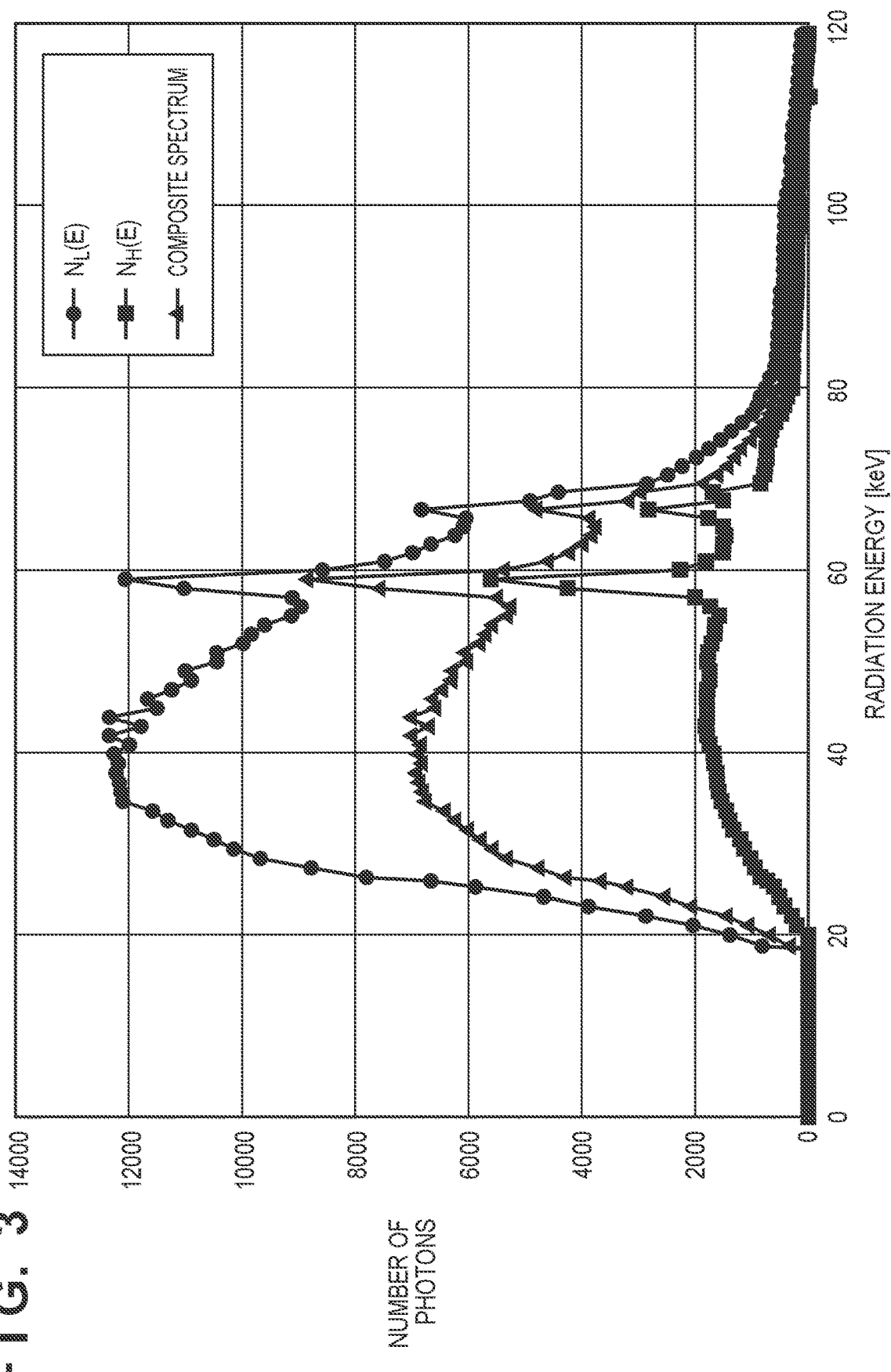
FIG. 3 is a graph showing an outline of a composite radiation spectrum according to the first embodiment.

In addition to the composition of radiation images, the composition unit 112 will obtain a composite radiation spectrum (to be also simply referred to as a "composite spectrum" hereinafter) that forms the composite radiation image 204 (Xproc). FIG. 3 is a graph showing the outline of the composite spectrum. Each radiation spectrum (to be also simply referred to as a "spectrum" hereinafter) includes information of the number of photons corresponding to the radiation energy level. In FIG. 3, the abscissa indicates the radiation energy level (KeV), and the ordinate indicates the number of photons. The storage unit 108 stores the spectra of different radiation energy levels.

As shown in FIG. 3, a composite spectrum $N_{proc}(E)$ can be obtained by calculating a radiation spectrum $N_L(E)$ and a radiation spectrum $N_H(E)$ which form $aX_L$ and $bX_H$, respectively, and averaging the calculated radiation spectra $N_L(E)$ and $N_H(E)$. If the values of the weighting factors a and b are known in advance, a spectrometer can be used to measure the low-energy radiation spectrum and the high-energy radiation spectrum, and a composite spectrum can be obtained based on the radiation spectra of the respective radiation energy levels measured in advance.

(S212: Noise Reduction Processing)

In step S212, the noise reduction processing unit 111 performs noise reduction processing on each material separation image 203 generated in step S210. The noise reduction processing unit Ill can perform noise reduction processing on the separated fat image or the separated bone image as a noise reduction processing target. For example, the noise reduction processing unit 11I can perform noise reduction processing on a fat image if a clearer bone image is to be obtained, and the noise reduction processing unit Ill can perform noise reduction processing on a bone image if a clearer fat image is to be obtained.

To exemplify a case in which a clearer bone image is to be obtained, an example in which noise reduction processing is performed on a fat image will be described here. The noise reduction processing unit 111 performs noise reduction processing on the fat image and obtains a smoothed fat image 205. The noise reduction processing unit 111 can apply, as a noise reduction method, structure-preserving noise reduction processing so the edge structure will not be lost. For example, a noise reduction method such as a bilateral filter, non-local means, an epsilon filter, or the like can be applied. In addition, for an image such as a fat image which has a few edge structures, the noise reduction processing unit 111 can apply a noise reduction method such as a Gaussian filter which will reduce high-frequency components.

(S213: Estimation of Noise-Reduced Bone Image)

In step S213, the image generating unit 110 will generate a noise-reduced material separation image (a bone image 206). More specifically, the image generating unit 110 will generate, based on equation (4) as follows, the noise-reduced bone image 206 from the composite radiation image 204 (Xproc: S211), obtained by compositing the low energy image 201 ($X_L$) and the high energy image 202 ($X_H$) captured by the FPD 102, and the noise-reduced fat image 205 (S212).

$$X_{proc} = \frac{\int_0^\infty N_{proc}(E)\exp\{-\mu_B(E)d_B - \mu_A(E)d_A\}EdE}{\int_0^\infty N_{proc}(E)EdE} \quad (4)$$

Where, μ represents the ray attenuation coefficient, d represents the thickness of the material, E represents the radiation energy, N(E) represents the radiation spectrum, a suffix proc represents composition, and suffixes A and B represent fat and bone, respectively.

Figure 2:
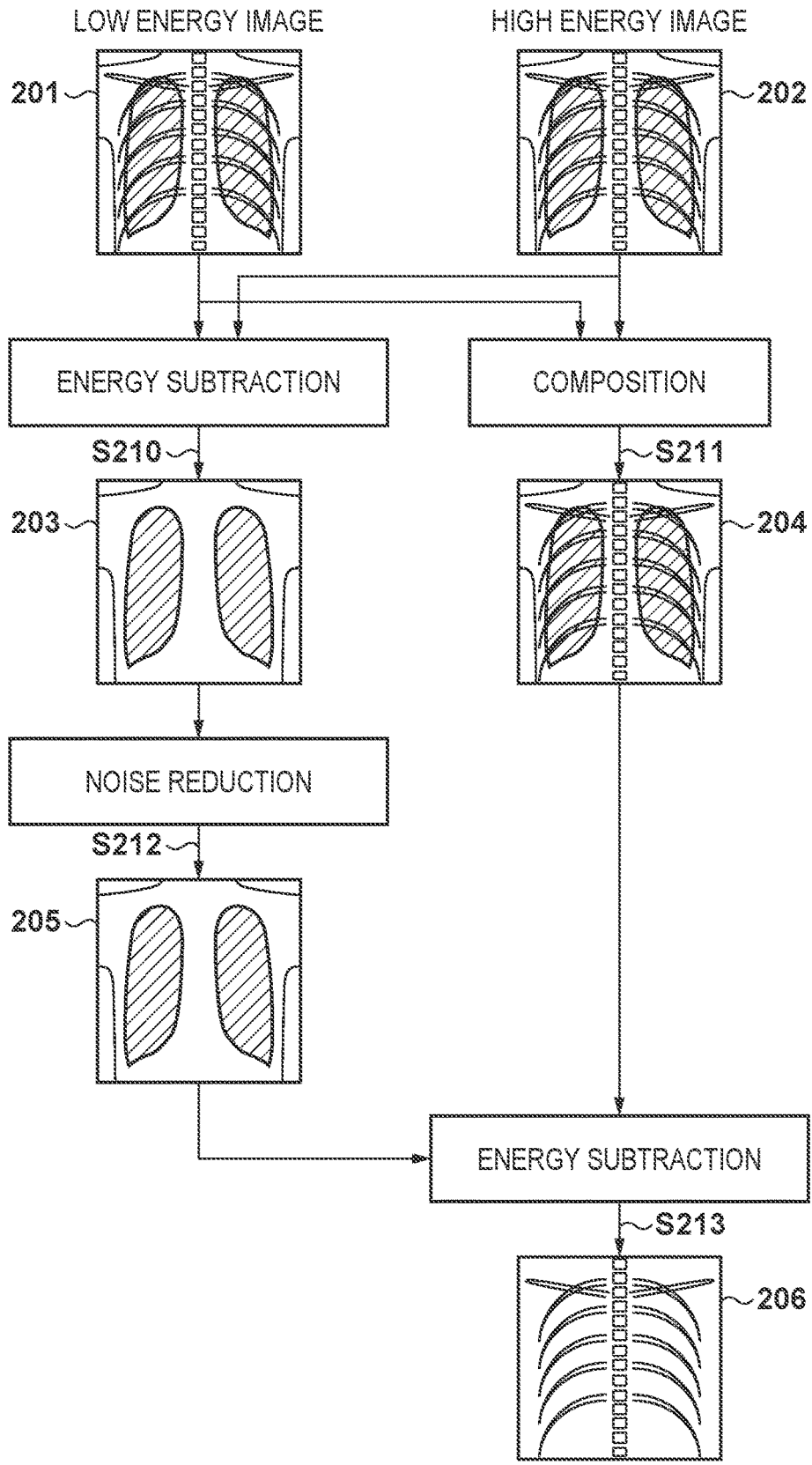
FIG. 2 is a view for explaining a procedure of processing in an image processing unit according to the first embodiment.

In the processing shown in FIG. 2, the image generating unit 110 generates, for example, a fat image as a first material characteristic image (S210), and the noise reduction processing unit 111 performs noise reduction processing on the fat image (S212). The image generating unit 110 uses the composite image (the composite radiation image 204 (Xproc)) obtained from the plurality of radiation images (S211), the first material characteristic image (the fat image) which has undergone noise reduction processing, and the composite spectrum (the composite spectrum $N_{proc}(E)$) obtained from different radiation energy spectra to generate a noise-reduced second material characteristic image (a bone image) (S213). That is, the image generating unit 110 generates, as the first material characteristic image, an image that indicates the thickness (or the density) of a first material (for example, fat) forming a plurality of materials, and generates, as a second material characteristic image, an image that indicates the thickness (or the density) of a second material (for example, bone) forming the plurality of materials.

Note that although fat and bone are used as examples of materials in this example of separation here, the materials to be separated are not limited to fat and bone, and arbitrary materials can be separated. The noise-reduced bone image 206 shown in FIG. 2 can be obtained by obtaining the thickness of the material (for example, the thickness $d_B$ of the bone) by solving equation (4) by an optimization method such as the Newton-Raphson method, the bisection method, or the like.

This embodiment is merely an example and is not limited to the procedure of processing described in FIG. 2. For example, a noise-reduced image can be obtained by performing noise reduction processing on an image, which has been obtained by adding the separated bone image and the separated fat image, and solving equation (4) to obtain the thickness of each material (the thickness $d_A$ of the fat or the thickness $d_B$ of the bone). Solving equation (4) to obtain the thickness of the material (the thickness $d_B$ of the bone) will allow a noise-reduced bone image to be obtained in the manner described above, and solving equation (4) to obtain the thickness of the material (the thickness $d_A$ of the fat) will allow a noise-reduced fat image to be obtained.

Furthermore, by preparing a plurality of images for each of the images (the low energy image 201 and the high energy image 202) obtained at different radiation energy levels, the embodiment can be applied to a case in which an object is to be separated into a plurality of materials (for example, a plurality of fat images and a plurality of bone images). In addition, the processing of FIG. 2 may be alternately repeated on each of the material characteristic images and noise reduction processing may be further performed on these images.

For example, the noise reduction processing unit 111 will execute noise reduction processing to reduce a noise component of the second material characteristic image (for example, a bone image) generated in step S213 (S212). Subsequently, the image generating unit 110 will use the composite image (S211, 204), the second material characteristic image whose noise component has been reduced, and the composite spectrum to further generate a noise-reduced first material characteristic image (for example, a fat image) (S213).

The image generating unit 110 will use the composite image (S211, 204), the noise-reduced first material characteristic image (S212, the fat image 205), and the composite spectrum to execute processing (first processing) to generate the noise-reduced second material characteristic image (S213, the bone image 206). In addition, the image generating unit 110 will use the composite image (S211, 204), the noise-reduced second material characteristic image (S212, the bone image 206), and the composite spectrum to execute processing (second processing) to generate the noise-reduced first material characteristic image (S213, the fat image 205). Subsequently, the image generating unit 110 will alternately execute the first processing and the second processing repeatedly.

In a case in which the processing of FIG. 2 is to be applied to a material identification image, the spatial distribution of an effective atomic number and the surface density can be obtained by solving equation (5) and equation (6) as follows.

$$X_L = \frac{\int_0^\infty N_L(E)\exp\{-\mu(Z_{eff}, E)D_{eff}\}EdE}{\int_0^\infty N_L(E)EdE} \quad (5)$$

$$X_H = \frac{\int_0^\infty N_H(E)\exp\{-\mu(Z_{eff}, E)D_{eff}\}EdE}{\int_0^\infty N_H(E)EdE} \quad (6)$$

In equation (5) and equation (6), E represents the energy, N(E) represents the radiation spectrum, $\mu(Z_{eff}, E)$ represents a mass attenuation coefficient of an effective atomic number $Z_{eff}$ and the energy E, and $D_{eff}$ represents a surface density. Also, suffixes H and L represent high energy and low energy, respectively. The unknown variables in equation (5) and equation (6) are the effective atomic number $Z_{eff}$ and the surface density $D_{eff}$. Hence, since images (a plurality of radiation images (a low energy image and a high energy image)) captured at two different radiation energy levels can be substituted into equation (5) and equation (6) to generate two independent equations, in a similar manner to a case in which the spatial distribution (material separation image) of thickness is obtained for each material, the values of the effective atomic number $Z_{eff}$ and the surface density $D_{eff}$ can be obtained by solving these two independent equations.

In addition, the composite radiation image 204 (Xproc) can be generated by using equation (3) as described above, and a noise-reduced material identification image can be generated by solving equation (7) as follows instead of equation (4).

$$X_{proc} = \frac{\int_0^\infty N_{proc}(E)\exp\{-\mu(Z_{eff}, E)D_{eff}\}EdE}{\int_0^\infty N_{proc}(E)EdE} \quad (7)$$

A noise-reduced material identification image (an image showing the distribution of the effective atomic number $Z_{eff}$ or the surface density $D_{eff}$) can be obtained by solving equation (7) by an optimization method such as the Newton-Raphson method, the bisection method, or the like.

E represents the energy, N(E) represents the radiation spectrum, $\mu(Z_{eff}, E)$ represents the mass attenuation coefficient of the effective atomic number $Z_{eff}$ and the energy E, and $D_{eff}$ represents the surface density. Suffix proc represents composition.

In the processing of FIG. 2, the image generating unit 110 will generate, for example, a surface density image as a first material characteristic image (S210), and the noise reduction processing unit 111 will perform noise reduction processing on the surface density image (S212).

The image generating unit 110 will use a composite image (the composite radiation image 204 (Xproc)) obtained from a plurality of radiation images (S211), the first material characteristic image (the surface density image) which has undergone noise reduction processing, and a composite spectrum (the composite radiation spectrum $N_{proc}(E)$) obtained from different radiation energy spectra to generate a noise-reduced second material characteristic image (an image showing the distribution of the effective atomic number) (S213). That is, the image generating unit 110 will generate a surface density image as the first material characteristic image (S210), and generate an effective atomic number image as the second material characteristic image (S213).

The present invention is not limited to this example. In a case in which the image generating unit 110 has generated an effective atomic number image as the first material characteristic image (S210) and the noise reduction processing unit 111 is to perform noise reduction processing on the effective atomic number image (S212), the image generating unit 110 will use a composite image (the composite radiation image 204 (Xproc)) obtained from a plurality of radiation images (S211), the first material characteristic image (the effective atomic number image) which has undergone noise reduction processing, and a composite spectrum (the composite radiation spectrum $N_{proc}(E)$) obtained from different radiation energy spectra to generate a noise-reduced second material characteristic image (surface density image) (S213). That is, the image generating unit 110 will generate, as the first material characteristic image, an image which shows the effective atomic number (S210), and generate a surface density image as the second material characteristic image (S213).

The effective atomic number of iodine, which is contained in a contrast agent or the like, is 53, the effective atomic number of barium is 56, and the effective number of stainless steel as a member used for catheter guide wires or the like is 26. In addition, the effective atomic number of titanium as a member used for stents is 22. By using the information of each effective atomic number, each material inside a human body (object) can be identified in accordance with the imaging technique.

The image generating unit 110 can use the information of each effective atomic number to generate an image in which each material inside the human body (object) is identified in accordance with the imaging technique, and the generated image can be used as a virtual monochromatic radiation image for other processing such as angiography (DSA: Digital Subtraction Angiography) that uses energy subtraction.

According to this embodiment, it is possible to reduce the influence of beam hardening and obtain material separation images in which noise has been reduced.

Second Embodiment

In the first embodiment, a predetermined time may be required to generate a material characteristic image because an optimization method is used for each pixel during arithmetic processing of energy subtraction. The second embodiment will describe an arrangement that can obtain a material characteristic image in a short time by storing the arithmetic processing result of energy subtraction in a table or the like in advance, and referring to the table during energy subtraction processing.

In the following description, assume that a description of parts similar to the first embodiment will be omitted and only components particular to the second embodiment will be described. The arrangement of this embodiment has an advantageous effect when "real-timeness" is required such as during fluoroscopy or the like.

Figure 5:
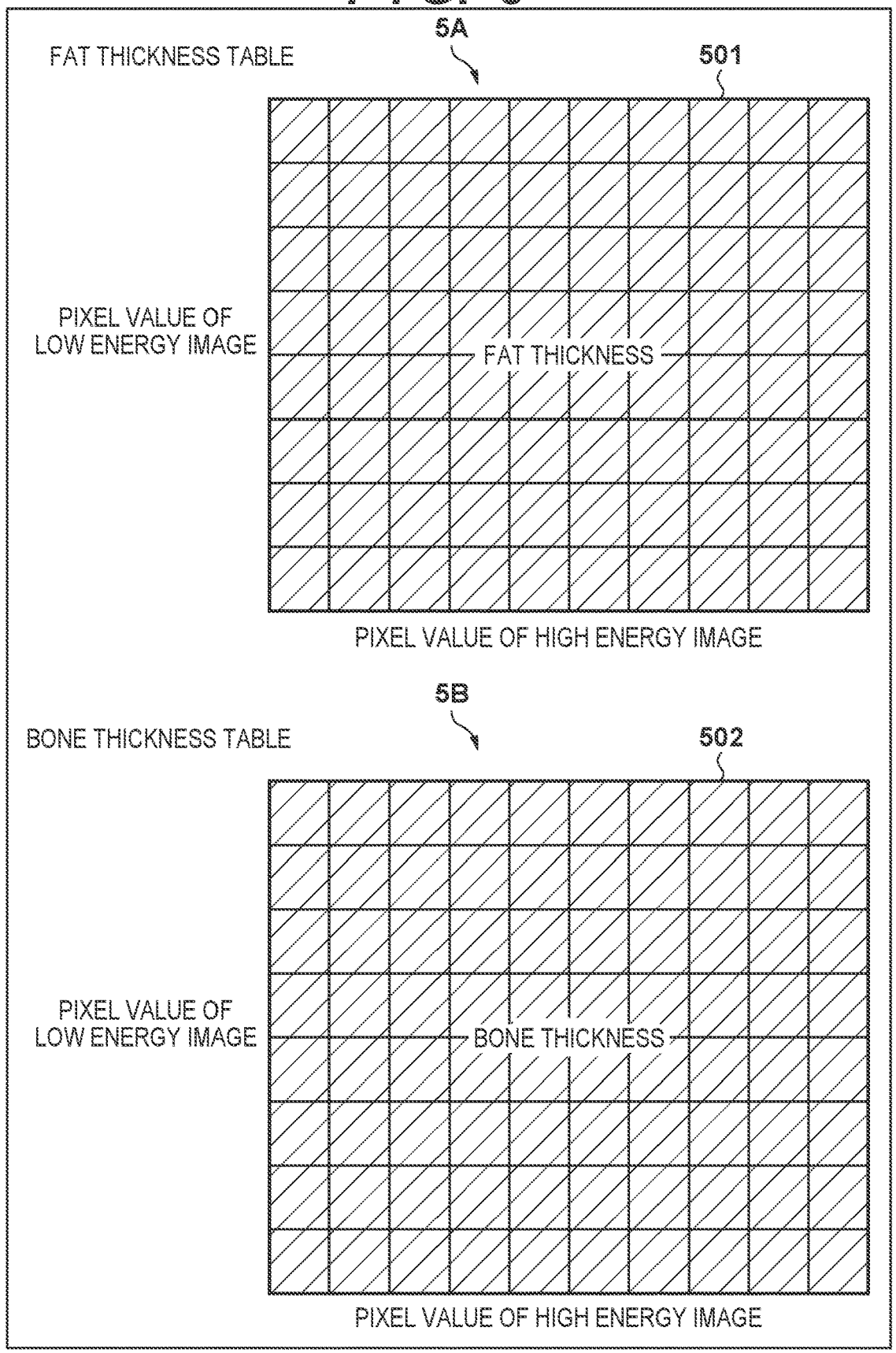
FIG. 5 is a view showing an example of a table for obtaining a material characteristic image according to the second embodiment.

In this embodiment, an image generating unit 110 will use a radiation energy spectrum to generate a material characteristic image of each material contained in a plurality of radiation images captured at different radiation energy levels, and will generate (S410) a first table (for example, a table 501 shown in 5A of FIG. 5 or a table 502 shown in 5B of FIG. 5) for outputting each material characteristic image corresponding to the captured plurality of radiation images.

A noise reduction processing unit 111 will reduce a noise component of a material characteristic image. That is, noise reduction processing unit 111 will reduce the noise component of a material characteristic image output from the first table (for example, the table 501 shown in 5A of FIG. 5 or the table 502 shown in 5B of FIG. 5).

Here, the image generating unit 110 will use a composite image (S412, 404) obtained from a plurality of radiation images, a first material characteristic image (S413, 405) which has undergone noise reduction processing, and a composite spectrum obtained from different radiation energy spectra to generate a second table (for example, 601 of FIG. 6) based on an arithmetic operation result obtained from generating a noise-reduced second material characteristic image (S414), and the image generating unit will output, from the second table (601), a second material characteristic image (S415, 406) corresponding to the composite image (404) and the first material characteristic image (405).

The procedure of processing performed by an image processing unit 109 according to the second embodiment will be described in detail next with reference to the flowchart shown in FIG. 4.

(S410: Generation of Table Related to Material)

In step S410, the image generating unit 110 will perform energy subtraction processing in advance to convert the arithmetic operation result into a table. For each of a plurality of materials forming a human body, the image generating unit 110 will obtain a low energy image ($X_L$) and a high energy image ($X_H$) by solving the simultaneous equations of equation (1) and equation (2) based on a possible combination of thicknesses of respective materials (for example, a combination of the thicknesses of fat as a first material and bone as a second material). An optimization method, for example, the Newton-Raphson method or the like can be used for the analysis of the two sets of simultaneous equations. The image generating unit 110 will generate the table 501, shown in 5A of FIG. 5, which represents a correspondence relationship between the low energy image ($X_L$), the high energy image ($X_H$), and the thickness of the first material (for example, fat) obtained from the simultaneous equations of equation (1) and equation (2), and will store the generated table in a storage unit 108. The image generating unit 110 will also generate the table 502, shown in 5B of FIG. 5, which represents a correspondence relationship between the low energy image ($X_L$), the high energy image ($X_H$), and the thickness of the second material (for example, bone) obtained from the simultaneous equations of equation (1) and equation (2), and will store the generated table in the storage unit 108.

The image generating unit 110 can improve the accuracy of a table by finely setting the step size in the ordinate and the abscissa of the table to be generated. Since table generation will require more time if the step size is finely set, the image generating unit 110 will also be able to arbitrarily set the step size of the table so that a desired accuracy will be obtained. The ordinate and the abscissa of the table may be set so that the values will be linearly set or logarithmically set. In addition, since the setting of the ordinate and the abscissa can be interpolated by using the value of a neighboring setting value, the setting of the ordinate and the abscissa may not be continuous.

(S411: Obtainment of Material Characteristic Images)

In step S411, the image generating unit 110 will use the tables (shown in 5A of FIGS. 5 and 5B of FIG. 5) generated in step S410, a low energy image 401 ($X_L$), and a high energy image 402 ($X_H$) to generate material separation images as material characteristic images. More specifically, the image generating unit 110 will obtain the material separation images (a fat thickness image and a bone thickness image) as the material characteristic images by referring to the tables (a fat thickness table (5A of FIG. 5) and a bone thickness table (5B of FIG. 5)) based on the value of each pixel of the low energy image 401 ($X_L$) and the high energy image 402 ($X_H$). The values of each table can be interpolated by a method, for example, bilinear interpolation, logarithmic interpolation, or the like.

(S412: Composition of Radiation Images and Radiation Spectra)

In step SS412, a composition unit 112 will generate, in a manner similar to step S211, a radiation image (to be referred to as a composite radiation image hereinafter) which has been composited based on a low-energy radiation image (the low energy image 401 ($X_L$)) and high-energy radiation image (the high energy image 402 ($X_H$)). That is, the composition unit 112 will generate the composite radiation image 404 (Xproc) from the low energy image 401 ($X_L$) and the high energy image 402 ($X_H$) based on equation (3).

(S413: Noise Reduction Processing)

In step S413, the noise reduction processing unit 111 will perform, in a manner similar to step S212, each material separation image 403 obtained in step S411. The noise reduction processing unit 111 can perform noise reduction processing on the separated fat image or the separated bone image as a noise reduction processing target. For example, if a clearer bone image is to be obtained, the noise reduction processing unit 111 can perform noise reduction processing on the fat image, and if a clearer fat image is to be obtained, the noise reduction processing unit 111 can perform noise reduction processing on the bone image. Here, as an example of obtaining a clearer bone image, the noise reduction processing unit 111 will perform noise reduction processing on the fat image to obtain the smoothed fat image 405.

(S414: Generation of Table for Obtaining Noise-Reduced Material Characteristic Image)

Figure 6:
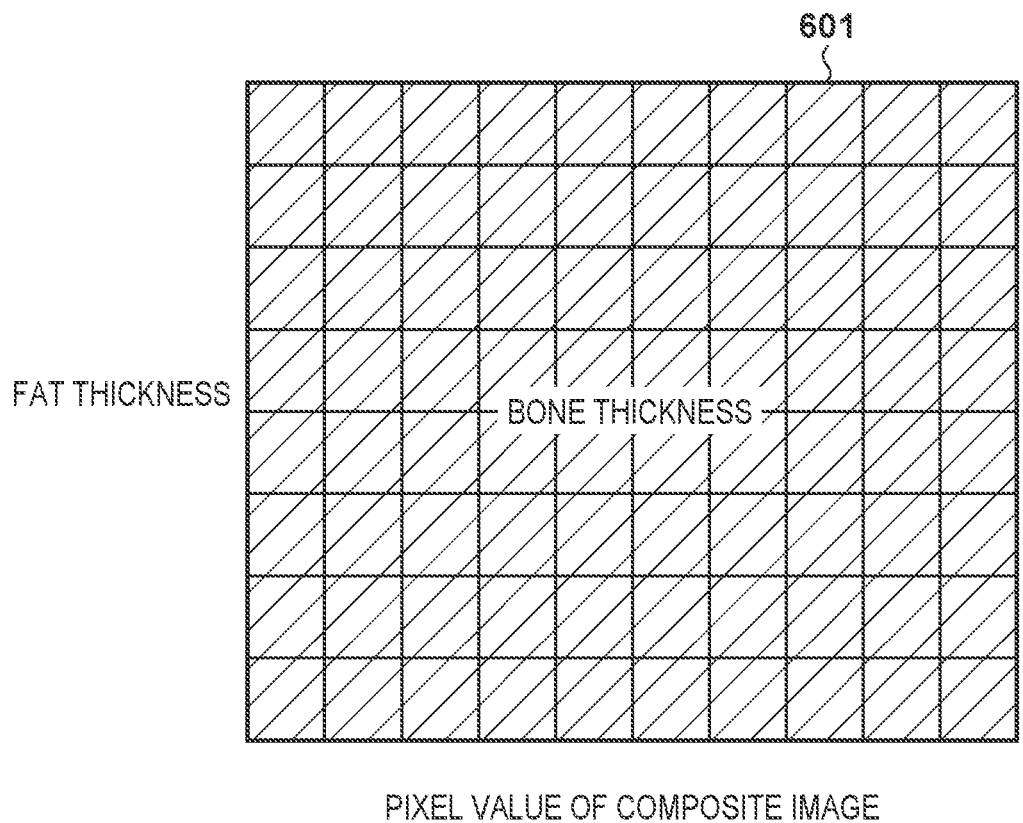
FIG. 6 is a view showing a table for obtaining a material characteristic image with reduced noise.

The image generating unit 110 will generate the table 601 in which the thicknesses of the first material (for example, fat), each pixel value of the composite radiation image, and the thickness of the second material (for example, bone) are associated, and will store the generated table in the storage unit 108. FIG. 6 is a view showing an example of the table 601 for obtaining a noise-reduced material characteristic image. The pixel values of the composite radiation image 404 (Xproc) are set in the abscissa, the thickness of the first material (fat) are set in the ordinate, and the distribution of the pixel values of the composite radiation image 404 (Xproc), the thickness of the first material (fat), and the thickness of the second material (bone) are associated.

As a more specific generation method of the table 601, the image generating unit 110 will obtain a thickness $d_B$ of the second material (bone) by solving equation (4) based on the combination of a thickness $d_A$ of the first material (fat) which may be found in a human body and each pixel value of the composite radiation image 404 (Xproc). Subsequently, the image generating unit 110 will generate the table 601 in which the obtained thickness $d_B$ of the second material (bone), each pixel value of the composite radiation image 404 (Xproc), and the thickness $d_A$ of the first material (fat) are associated.

(S415: Obtainment of Noise-Reduced Bone Image)

In step S415, the image generating unit 110 will use the table 601 generated in step S414, the composite radiation image 404 (Xproc), and the image (the smoothed first material characteristic image 405) of the thickness of the first material (fat) which had undergone noise reduction in step S413 to obtain the image (the second material characteristic image 406) of the thickness of the second material (bone) as a material characteristic image. The image generating unit 110 can refer to the table 601 to obtain the thickness $d_B$ of the second material (bone) based on the thickness $d_A$ of the first material (fat) which has undergone noise reduction in step S413 and each pixel value of the composite radiation image 404 (Xproc), and can obtain a noise-reduced bone image based on the obtained thickness $d_B$ of the second material (bone).

Figure 4:
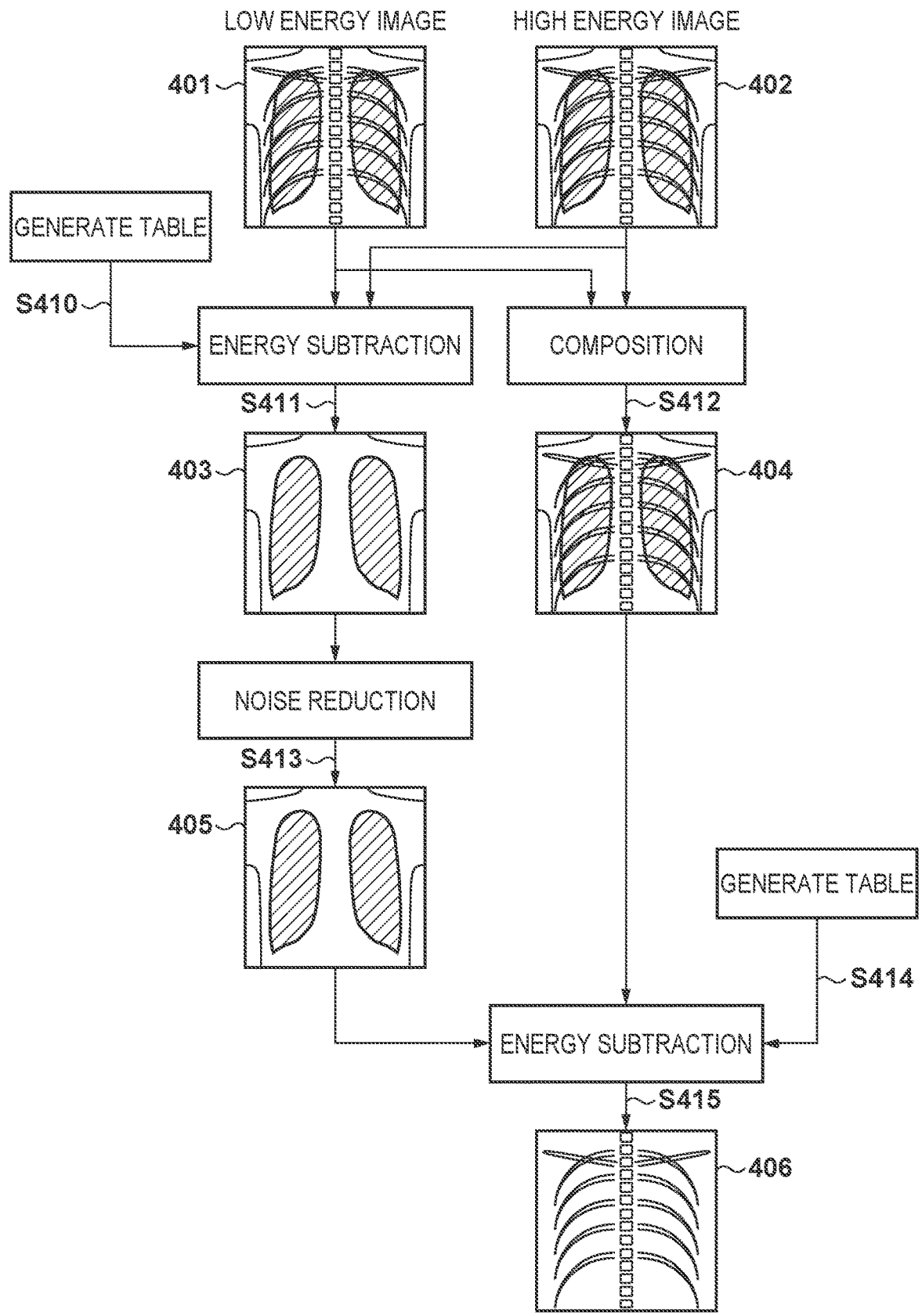
FIG. 4 is a view for explaining a procedure of processing of an image processing unit according to the second embodiment.

According to the processing described in FIG. 4, by referring to the tables 501 and 502 in step S410, it will be possible to obtain a material separation image as a material characteristic image while reducing the arithmetic operation load based on equation (1) and equation (2). In addition, by referring to the table 601 in step S414, it will be possible to obtain a material separation image as a noise-reduced material characteristic image while reducing the arithmetic operation load based on equation (4). According to the processing of the second embodiment described in FIG. 4, the processing can be applied to moving image capturing which requires faster image processing.

Comparison of Image Processing Results

Figure 7:
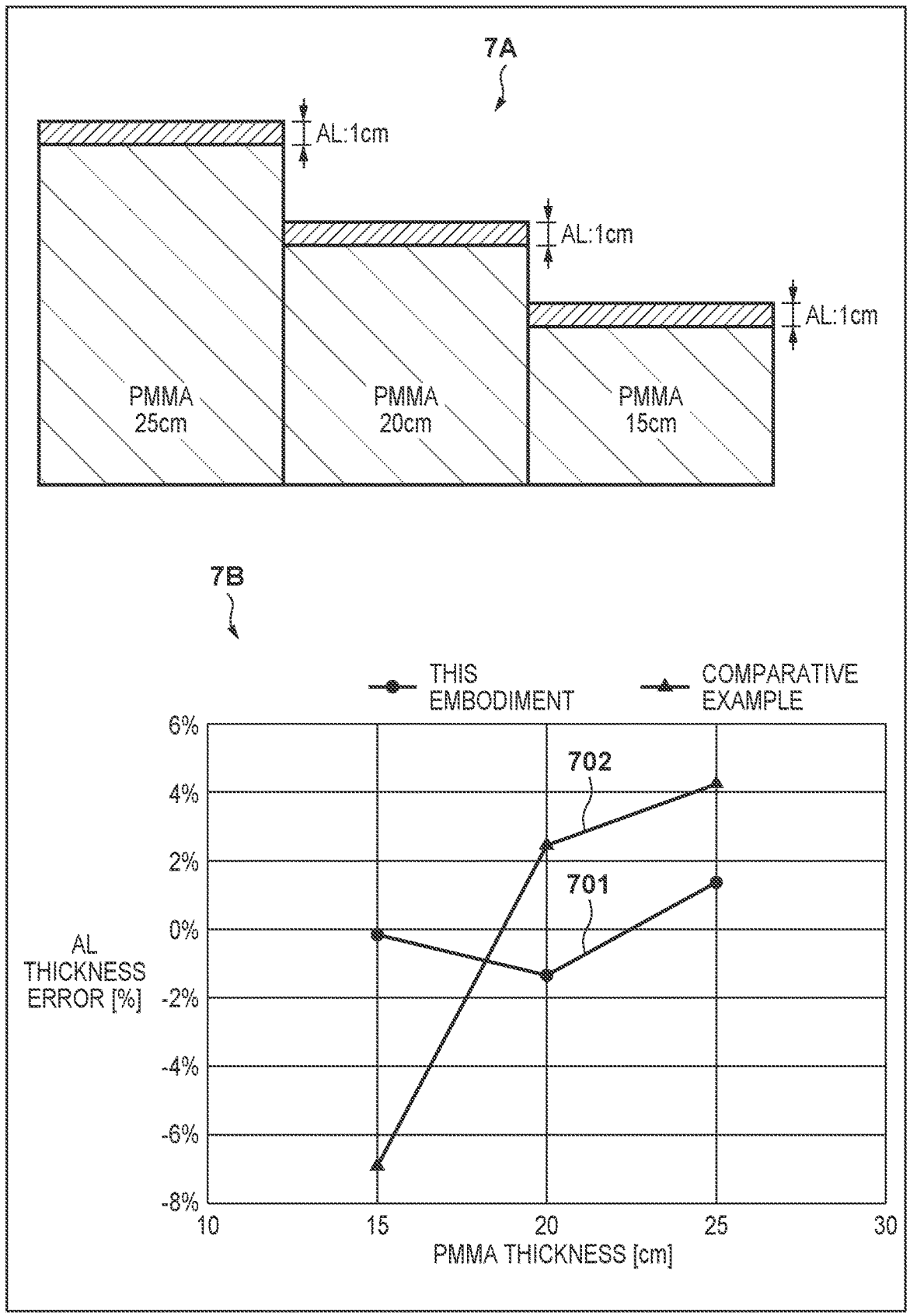
FIG. 7 is a view showing an example of the effects of the embodiments of the present invention.

The accuracy of the material characteristic images obtained according to the embodiments (the first embodiment and the second embodiment) of the present invention will be described. FIG. 7 is a view showing an example of the effect of each embodiment of the present invention. 7A of FIG. 7 is a view showing an example of the arrangement of a phantom for measuring the effect. The phantom shown in 7A of FIG. 7 is used to obtain a low-energy radiation image (low energy image) and a high-energy radiation image (high energy image), and a waveform 701 of 7B of FIG. 7 is obtained as a result of obtaining the thickness of each material forming the phantom based on the processing of an embodiment (for example, the first embodiment or the second embodiment) of the present invention. A waveform 702 of 7B of FIG. 7 shows, as a comparative example, a result obtained by using an energy subtraction method disclosed in PTL 1. The phantom is made of acrylic resin (PMMA) and aluminum (AL). The acrylic resin (PMMA) corresponds to fat as a soft material and the aluminum (AL) corresponds to bone as a hard material. In the arrangement of the phantom, the thickness of the aluminum (AL) is constant at 1 cm. The acrylic resin (PMMA) has three kinds of thicknesses which are 15 cm, 20 cm and 25 cm.

In 7B of FIG. 7, the abscissa represents the thickness of acrylic resin (PMMA), and the ordinate represents an error with respect to the thickness of 1 cm of aluminum (AL). As shown in the waveform 702 of 7B of FIG. 7, in the energy subtraction method disclosed in PTL 1, the error in the thickness of aluminum (AL) varies with respect to the thickness of the acrylic resin (PMMA) in a range of −7% to +4%. On the other hand, as shown in the waveform 701 of 7B of FIG. 7, in the processing according to the embodiment of the present invention, the error in the thickness of aluminum (AL) with respect to the thickness of acrylic resin (PMMA) falls within a range of approximately ±1%.

Error can be reduced in the processing according to each embodiment of the present invention compared to the processing of PTL 1 as the related art, and each embodiment of the present technique is effective when measurement requiring quantitative properties are to be performed in image processing. In particular, the embodiments of the present invention are characterized by good quantitative properties even if the thickness of acrylic resin (PMMA) changes and beam hardening occurs.

According to the present invention, a material characteristic image with reduced noise and good quantitative properties can be obtained.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:
1. An image processing apparatus comprising:
at least one of (a) one or more processors connected to one or more memories storing a program including instructions executed by the one or more processors and (b) circuitry, configured to function for:
generating, by using a radiation energy spectrum, a material characteristic image of a material contained in a plurality of radiation images captured by different radiation energies; and
reducing a noise component of the material characteristic image,
wherein the at least one of (a) one or more processors and (b) circuitry is configured to function for generating a second material characteristic image by using (1) a composite image obtained from the plurality of radiation images, (2) a first material characteristic image in which the noise component has been reduced, and (3) information indicative of a relationship between the second material characteristic image, the composite image, and the first material characteristic image.

2. The image processing apparatus according to claim 1, wherein the at least one of (a) one or more processors and (b) circuitry is configured to function for generating the second material characteristic image by using (1) the composite image, (2) the first material characteristic image, and (3) a table that is generated as the information.

3. The image processing apparatus according to claim 1, wherein the material characteristic image is a material separation image obtained by separating a plurality of materials contained in the plurality of radiation images.

4. The image processing apparatus according to claim 3, wherein the at least one of (a) one or more processors and (b) circuitry is configured to function for:
generating, as the first material characteristic image, an image that indicates one of the thickness and the density of a first material which forms the plurality of materials; and
generating, as the second material characteristic image, an image that indicates one of the thickness and the density of a second material which forms the plurality of materials.

5. The image processing apparatus according to claim 1, wherein the material includes fat as a soft material and bone as a hard material that form an object.

6. The image processing apparatus according to claim 1, the at least one of (a) one or more processors and (b) circuitry is configured to function for:
(1) generating, as the first material characteristic image, an image indicating a distribution of a surface density of a material contained in the plurality of radiation images, and generating, as the second material characteristic image, an image indicating a distribution of an effective atomic number of a material contained in the plurality of radiation images, or
(2) generating, as the first material characteristic image, an image indicating a distribution of an effective atomic number of a material contained in the plurality of radiation images, and generating, as the second material characteristic image, an image indicating a distribution of a surface density of a material contained in the plurality of radiation images.

7. The image processing apparatus according to claim 1, wherein the first material characteristic image and the second material characteristic image are material identification images that indicate a distribution of an effective atomic number and a surface density of a material contained in the plurality of radiation images, and
wherein the at least one of (a) one or more processors and (b) circuitry is configured to function for generating an image for identifying a material contained inside an object by using information of the effective atomic number.

8. The image processing apparatus according to claim 1, wherein the at least one of (a) one or more processors and (b) circuitry is further configured to function for causing a display unit to display the generated material characteristic image.

9. The image processing apparatus according to claim 1, wherein the at least one of (a) one or more processors and (b) circuitry is further configured to function for generating the first material characteristic image and the second material characteristic image by using the plurality of radiation images obtained by one radiation irradiation operation.

10. The image processing apparatus according to claim 1, wherein the spectrum includes information of a number of photons corresponding to radiation energy.

11. The image processing apparatus according to claim 1, wherein the at least one of (a) one or more processors and (b) circuitry is further configured to function for storing the spectrum for each different radiation energy.

12. The image processing apparatus according to claim 1, wherein the at least one of (a) one or more processors and (b) circuitry is further configured to function for generating the composite image by executing weighted addition processing on the plurality of radiation images.

13. The image processing apparatus according to claim 1, wherein the at least one of (a) one or more processors and (b) circuitry is configured to function for:
calculating a dose or a number of photons during capturing of the plurality of radiation images;
setting, based on one of a ratio of the calculated dose and a ratio of the calculated number of photons, a weighting factor used in addition processing on the plurality of radiation images; and
obtaining a composite spectrum (a) based on the weighting factor and the radiation spectrum of each radiation energy that has been measured, or (b) by averaging spectra forming the plurality of the radiation images.

14. The image processing apparatus according to claim 1, wherein the at least one of (a) one or more processors and (b) circuitry is configured to function for:
reducing a noise component of the second material characteristic image to obtain a reduced-noise-component second material characteristic image; and
generating a first material characteristic image with further reduced noise component, by using (1) the composite image, (2) the reduced-noise-component second material characteristic image, and (3) a composite spectrum obtained from spectra of the different radiation energies.

15. The image processing apparatus according to claim 14, wherein the at least one of (a) one or more processors and (b) circuitry is configured to function for alternately executing, repeatedly:
processing to generate a second material characteristic image with further reduced noise component by using (1) the composite image, (2) the first material characteristic image with further reduced noise component, and (3) the composite spectrum; and
processing to generate a first material characteristic image with still further reduced noise component by using (1) the composite image, (2) the second material characteristic image with further reduced noise component, and (3) the composite spectrum.

16. An image processing apparatus comprising:
at least one of (a) one or more processors connected to one or more memories storing a program including instructions executed by the one or more processors and (b) circuitry, configured to function for:
obtaining a material characteristic image related to a material contained in a plurality of radiation images captured by different radiation energies;
obtaining a composite image obtained from the plurality of radiation images;
obtaining information indicative of a relationship between a new material characteristic image, the composite image, and the material characteristic image; and
obtaining the new material characteristic image by using (1) the obtained material characteristic image, (2) the obtained composite image, and (3) the obtained information.

17. An image processing method comprising:
reducing a noise component of a first material characteristic image of a material contained in a plurality of radiation images captured by different radiation energies; and generating a second material characteristic image by using (1) a composite image obtained from the plurality of radiation images, (2) the first material characteristic image, and (3) information indicative of a relationship between the second material characteristic image, the composite image, and the first material characteristic image.

18. A non-transitory computer-readable storage medium storing a program for causing a computer to execute the method according to claim 17.

19. The image processing apparatus according to claim 1, wherein the at least one of (a) one or more processors and (b) circuitry is configured to function for obtaining a thicknesses of a second material in the second material characteristic image by inputting, to a table, (1) a pixel value of the composite image and (2) a thicknesses of a first material in the first material characteristic image, and wherein the table indicates a distribution of the thicknesses of the second material in a second material characteristic image with which the pixel value of the composite image and the thicknesses of the first material in the first material characteristic image are associated.

20. The image processing apparatus according to claim 1, wherein the at least one of (a) one or more processors and (b) circuitry is configured to function for generating, without using the information, the second material characteristic image by using information regarding a difference between (i) a multiplication result of the first material characteristic image and a composite spectrum obtained from spectra of the different radiation energies and (ii) the composite image.

\* \* \* \* \*